United States Patent [19]

Heusser

[11] 3,951,321

[45] Apr. 20, 1976

[54] METHOD OF, APPARATUS FOR, TRANSPORTING YARNS THROUGH MEASURING UNITS

[75] Inventor: Eduard Heusser, Uster, Switzerland

[73] Assignee: Zellweger, Ltd., Switzerland

[22] Filed: Sept. 25, 1974

[21] Appl. No.: 509,220

[30] Foreign Application Priority Data

Sept. 26, 1973 Switzerland.................... 13804/73

[52] U.S. Cl.................................. 226/97; 57/77.3
[51] Int. Cl.²............................................. B65H 17/32
[58] Field of Search............ 226/7, 97, 45; 73/37.7; 57/77.3, 77.33, 77.35, 77.37, 1 R; 340/259; 200/61.13, 61.18; 250/219 S

[56] References Cited
UNITED STATES PATENTS

| | | | |
|---|---|---|---|
| 2,173,789 | 9/1939 | Nikles | 226/97 X |
| 2,497,017 | 2/1950 | Shann | 200/61.13 |
| 2,990,671 | 7/1961 | Bunting | 57/77.3 |
| 3,613,347 | 10/1971 | Carruthers | 57/1 R |

*Primary Examiner*—Richard A. Schacher
*Attorney, Agent, or Firm*—Craig & Antonelli

[57] ABSTRACT

A method and apparatus for transporting yarns, especially filaments, through measuring units provides for driving the yarn from a yarn supply to a measuring point by means of delivery rollers disposed upstream of the measuring point in the direction of travel of the yarn and pulling on the yarn downstream of the measuring point to apply a predetermined amount of tension to the yarn, the pulling of the yarn being effected by a nozzle acting in the manner of an injector producing an airstream entraining the yarn so as to pull and also selectively rotate the yarn to apply a twist thereto.

2 Claims, 4 Drawing Figures

METHOD OF, APPARATUS FOR, TRANSPORTING YARNS THROUGH MEASURING UNITS

This invention relates to the transporting of yarns, especially filaments, through measuring units.

It is known that textile products, especially yarns, can be tested with regard to their cross-section over considerable lengths by means of measuring systems, for example with optical or capacitive means which probe the cross-section of the yarn and reproduce the corresponding fluctuations in cross-section in the form of changes in the electrical measuring signal which is generated thereby.

Hitherto, yarns have been carried through the measuring zone by means of delivery rollers which, driven at a given rotational speed, move the yarn to be tested forward at a constant speed. This arrangement has proved to be entirely suitable for the transport of yarns made of natural fibers, for example of cotton or wool. However, in the case of synthetic filaments, the use of a delivery arrangement of this kind gives rise to certain difficulties.

Filaments of man-made fibers are extremely elastic and stretchable. They are wound under tension into relatively large packages and are off wound by traction in the direction of the bobbin axis, so that the layers of filaments lying firmly on top of one another have to be released from one another. This results in irregular traction and, hence, in a variable elongation which is reflected in a variable crosssection of the filament. The basically low cross-sectional uniformity of the filaments calls for high sensitivity on the part of the measuring apparatus, so that the elongation-induced changes in cross-section appear to substantially the same extent as the actual material-related changes in cross-section and, as a result, create a false impression of increased, total irregularity. Although attempts have been made to eliminate or at least reduce tension-induced changes in elongation by using various types of filament brakes, none of these attempts has been really successful.

Another disadvantage of known apparatus results from arranging the delivery rollers after the measuring zone in that with such an arrangement the material being tested leaving the delivery rollers tends to adhere to parts of the measuring apparatus. That is especially the case with highly electrostatic filaments. In such a case, it is necessary to provide either winding units, which rewind the test material after it has left the delivery rollers, or an air-blast or evacuation unit which carries the tested material into a collecting vessel.

Another way of obtaining a signal more accurately corresponding to the material cross-section of filaments is to impart a so-called false-twist to the test material in the vicinity of the measuring zone in order to establish the cross-sectional form of the filament in the measuring zone. Both optical and capacitive measuring systems release different signals, depending on how the generally band-form material (in the case of filaments) is oriented in the measuring zone. If this orientation changes when the filament passes through the measuring zone, additional fluctuations in the measuring signal which are not caused by the cross-sectional form of the filament are superimposed upon the signal. Wrong indications of this kind are avoided by virtue of the false-twist in the filament which has to be applied by additional means.

An object of the present invention is to obviate these disadvantages. Accordingly, the present invention provides a method of transporting yarns, especially filaments, through measuring units, in which the yarn is withdrawn from a supply package by means of delivery rollers arranged in front of the measuring unit, as seen in the direction of travel of the yarn, and the yarn issuing behind the delivery rollers is carried along by an airstream oriented substantially in the direction in which the filament passes through the measuring unit, and, at the same time, is subjected to a uniform, adjustable tension thereby.

The invention also provides an apparatus for carrying out the method and comprising a pair of delivery rollers arranged in front of the measuring unit, and a nozzle for producing a uniform, adjustable tension in the vicinity of the measuring unit, downstream thereof in the direction of travel of the filament.

In a practical embodiment of the method according to the invention, the airstream can be produced either by the outflow of air from a pipe under excess air pressure, or by the suction effect of a pipe under reduced air pressure.

In one advantageous embodiment of the invention, the pipe of a pneumatic accelerator is fitted with a regulating valve by which the rate of airflow and hence the tension applied to the yarn to be tested are made adjustable.

Another advantage of an apparatus according to the invention is obtained when the pipe for producing the airstream is introduced tangentially into the nozzle. As a result of such an arrangement, the air in the nozzle forms a vortex and, in doing so, additionally imparts a twist to the yarn to be tested without requiring any mechanical contact with the yarn. The feedpipes can be introduced into the nozzle from the left and/or from the right and connected by means of a threeway cock, so that a dextrorotatory or levorotatory vortex may be formed, according to requirements, and a false-twist directed to the left or right (S- or Z-twist) may be thereby additionally imparted to the yarn.

This is of particular advantage so far as ribbon-like filaments are concerned, because an average value of the cross-section is formed in this way in measuring zone, thereby eliminating the so-called form effect of noncircular cross-sections of the kind in question.

One embodiment of the invention will now be described by way of example with reference to the accompanying drawings, in which.

Figure 1:
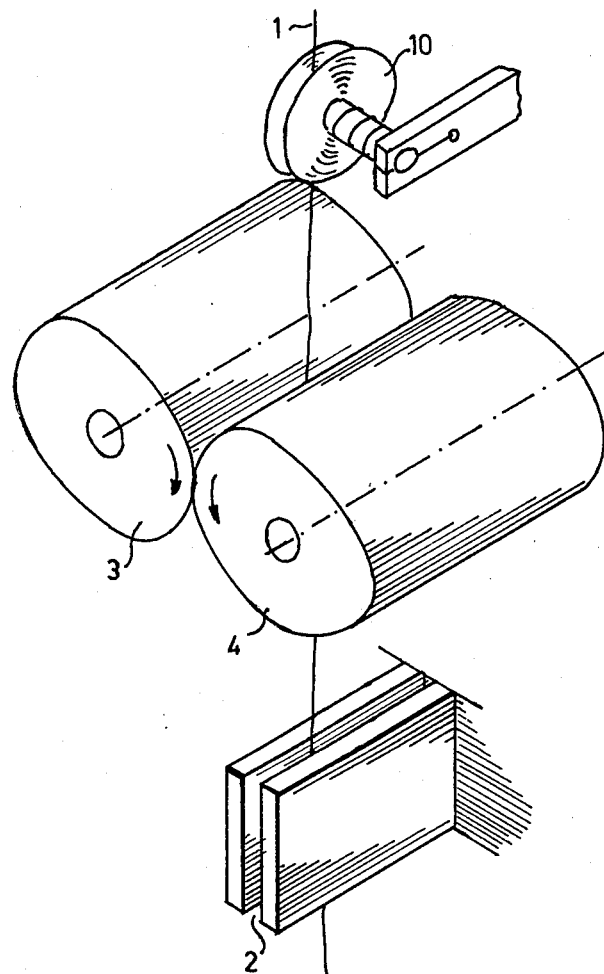
FIG. 1 is a perspective view of a delivery arrangement in accordance with one embodiment of the present invention.

Referring to FIG. 1, a measuring unit 2, which can be in the form, for example, of a plate capacitor, measures the cross-section of a yarn 1 passed through it in known manner because of the influence which the yarn has on the capacitance. It is of course also possible to use other known measuring systems, for example, optical or acoustical measuring systems. The yarn 1 is wound off a supply package (not shown) by means of motordriven delivery rollers 3 and 4. A yarn brake 10 of known type can be arranged before the point at which the yarn enters the delivery rollers. The rotational speed or peripheral speed of the delivery rollers 3, 4 determines the rate at which the yarn passes through the measuring unit 2. The delivery rollers can be made to rotate at desired rotational speeds through a conventional drive gear system, such as gear unit 5 coupled to drive unit 6, both known per se. The rollers arrest any changes in the tension of the yarn and prevent such changes from producing an influence in the measuring zone.

In the absence of further measures, the unguided yarn 1 issuing below the delivery rollers 3, 4 would very likely be deposited onto the measuring unit in a tangled heap without passing between the plates. Accordingly, another tensioning means has to be provided below the measuring unit 2 for imparting a predetermined tension to the yarn 1 in the measuring unit. In accordance with the present invention, this tensioning means is provided in the form of a small nozzle 7 which is operated in the manner of an injector with the airstream entering laterally and issuing downwards. The yarn 1 is entrained downwards by this airstream, so that it is subjected to a gentle, but sufficient and substantially constant, tension which provides for smooth passage of the yarn through the measuring unit 2. This yarn tension is not sufficient to give rise to any appreciable elongation, with the result that no false cross-sectional values are presented to the measuring unit 2.

Figure 2:
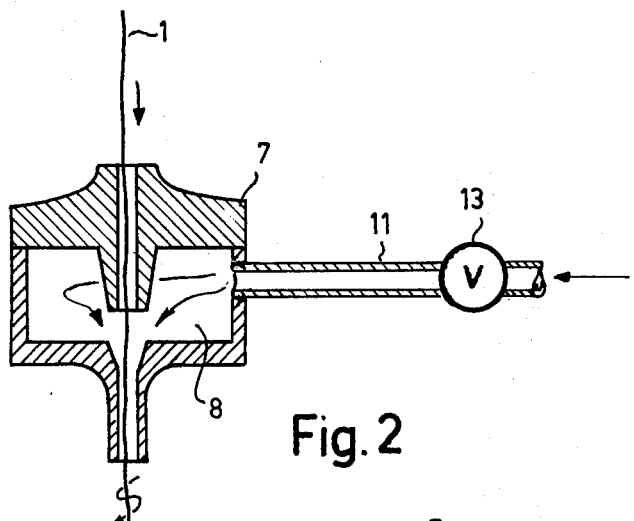
FIG. 2 is a section through a nozzle of the type which may be used with the present invention.

FIG. 2 is a section through a nozzle 7 which comprises a compartment 8 having a configuration such that the air flowing in through the valve 13 and the pipe 11 is deflected and issues through the orifice 15. The strength of the airstream or the rate of flow of the issuing air and, hence, the level of tension acting on the yarn 1 can be adjusted by means of a controllable valve 13 fitted into the air pipe 11. The measured yarn 1 issuing from the nozzle 7 is collected for example in a collecting vessel 9 as seen in FIG. 1.

For measuring filaments in capacitive or optical measuring units, the effect of the generally band-form cross-section has to be compensated in the measuring zone. This is achieved in known manner by imparting a so-called false-twist to the yarn, converting the ribbon form of the test material into a spiral form in the measuring zone. A mechanically driven twisting tube arranged in the immediate vicinity of the measuring unit is normally used for producing the aforementioned false-twist in known arrangements.

Figures 3, 4:
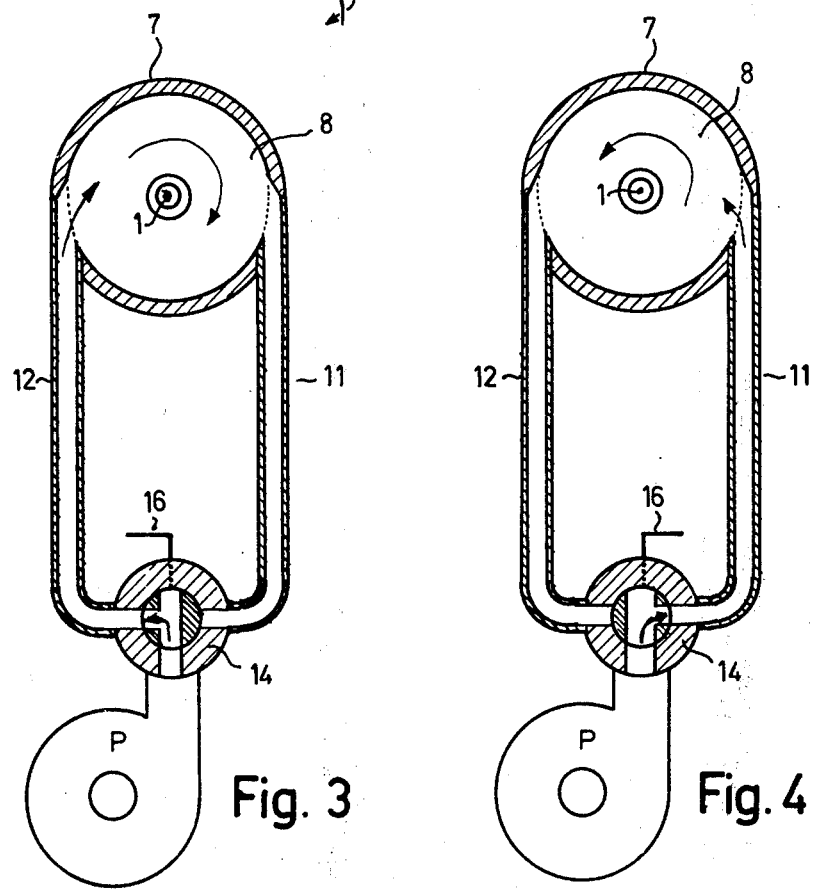
FIG. 3 is a partial sectional view through the nozzle and valve of a second embodiment illustrating the airflows for a dextrorotatory vortex.
FIG. 4 is a partial sectional view similar to FIG. 3 illustrating the airflows for a levorotatory vortex in the nozzle.

The method and apparatus of this invention enable a false-twist to be produced without additional means. To this end, as seen in FIGS. 3 and 4, the point at which the airline opens into the compartment 8 of the nozzle 7 is tangentially arranged so that the inflowing air forms a vortex and, by entraining the yarn 1, twists it. Since this twist can be directed to the left or to the right (Z- or S-twist), two lines 11, 12 open tangentially into the nozzle 7, being connected in common by a three-way clock 14 to a fan unit P. The air is steered through the left-hand line 11 or through the right-hand line 12, depending upon the position of the pivotal lever 16, and a correspondingly directed twist is thereby obtained. The strength of the airstream can be adjusted according to the selected opening of the cock.

In another position of the three-way cock 14, air can be admitted simultaneously into both lines 11, 12, so that no vortex is formed in the nozzle compartment 8 and, hence, no false-twist imparted to the yarn 1.

Although only a single embodiment of the invention has been specifically described above, it should be appreciated that many modifications can be made without departing from the spirit and scope of the invention. For example, nozzle 7 can be driven by means of a suction effect rather than an increased pressure effect. In this arrangement, air pipe 11 is connected by a valve 13 to a source of subatmospheric pressure. In addition, compartment 8 is so designed that a reduction in pressure therein will cause yarn 1 to be sucked into compartment 8 and thereafter ejected therefrom via nozzle 15. Operating with a positive gas pressure, i.e. that is with pressures over one atmosphere, it is preferred since the pressure differential of greater than one atmosphere can be employed. Moreover, a positive gas pressure enables the production of a cyclone effect as described above in connection with FIGS. 3 and 4.

The foregoing description has been presented for illustrative purposes only and is not intended to limit the invention in any way. All reasonable modifications not specifically set forth or intended to be included within the scope of the present invention, which is to be limited only by the following claims.

What is claimed is:

1. An apparatus for transporting yarns, especially filaments, through a measuring unit, comprising: a measuring unit; means for delivering a yarn to said measuring unit including a pair of delivery rollers preceeding the measuring unit in the direction of travel of the yarn; nozzle means engaging the yarn downstream of said measuring unit for applying a uniform adjustable tension to the yarn in the measuring unit, said nozzle means including a nozzle having an air chamber, a three-way cock and a pair of airlines tangentially opening into the nozzle chamber on opposite sides thereof and being connected to respective outlets of said three-way cock; and air supply means for applying air under pressure to said cock so that a flow of air can be selectively applied through the line opening tangentially into the nozzle chamber from one side or from the other side to produce a vortex of air therein which will impart an S- or Z-twist to the yarn, respectively.

2. An apparatus as claimed in claim 1, wherein said three-way cock has a neutral position in which air is supplied simultaneously to both airlines, so that no air vortex is formed in the nozzle and, hence, no twist imparted to the yarn.

* * * * *